United States Patent [19]
Leighton

[11] Patent Number: 6,103,518
[45] Date of Patent: Aug. 15, 2000

[54] INSTRUMENT FOR CONSTRUCTING TISSUE ARRAYS

[75] Inventor: Stephen B. Leighton, Silver Spring, Md.

[73] Assignee: Beecher Instruments, Silver Spring, Md.

[21] Appl. No.: 09/263,304

[22] Filed: Mar. 5, 1999

[51] Int. Cl.[7] .................................................. C12M 1/36
[52] U.S. Cl. .................................... 435/286.3; 435/284.1; 435/286.2; 435/307.1; 435/307.9; 422/63
[58] Field of Search ................. 422/63, 68.1; 435/284.1, 435/286.1, 286.2, 286.3, 307.1, 309.1

[56] References Cited

U.S. PATENT DOCUMENTS

| | | | |
|---|---|---|---|
| 4,684,613 | 8/1987 | Barrere et al. | 435/301 |
| 4,979,093 | 12/1990 | Laine et al. | |
| 5,355,304 | 10/1994 | DeMoranville et al. | |
| 5,355,439 | 10/1994 | Bernstein et al. | |
| 5,675,715 | 10/1997 | Bernstein et al. | |

OTHER PUBLICATIONS

Juha Kononen, et al.; Tissue microarrays for high-throughput molecular profiling of tumor specimens; Nature Medicine; vol. 4; No. 7; Jul. 1998.

*Primary Examiner*—David A. Redding
*Attorney, Agent, or Firm*—Pendorf & Cutliff

[57] ABSTRACT

A simple, robust and precise instrument for constructing tissue arrays. The instrument includes multiple punches mounted on a punch platform, the punch platform displaceable between precisely defined positions. Mechanical détentes or stops are provided which mechanically arrest the movement of the punch platform in the precisely defined positions. This arrangement greatly saves time and improves accuracy over use of conventional precision linear positioning means. By the simple step of moving the punch platform from a first position to a second position, either punch can be quickly brought into operating position (and the other moved into a non-interfering position) by either manually or by automatic means, making it possible to quickly alternate from one punch to the other.

18 Claims, 4 Drawing Sheets

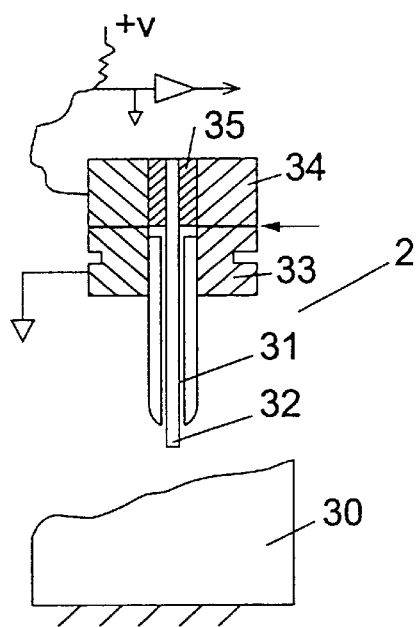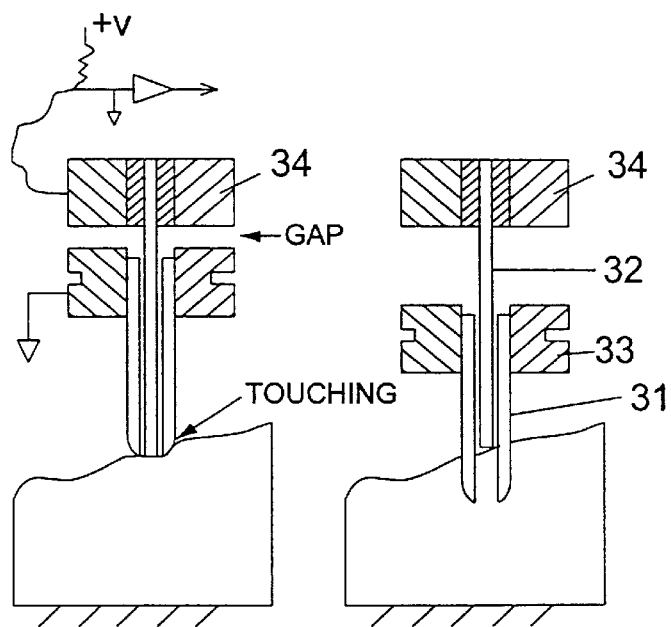
Fig. 2a     Fig. 2b     Fig. 2c
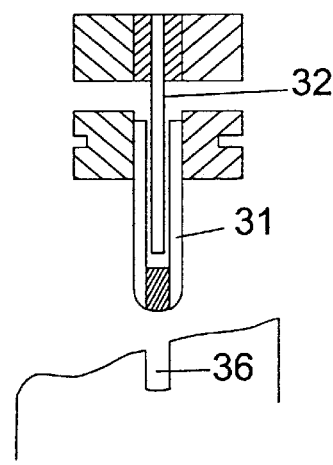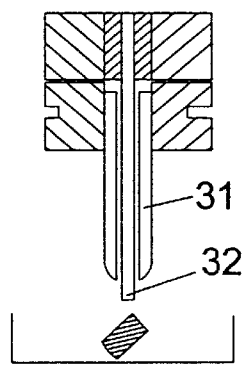
Fig. 2d     Fig. 2e

INSTRUMENT FOR CONSTRUCTING TISSUE ARRAYS

The United States government may have certain rights in the present invention pursuant to Grant No. 273-MH-801143-2 awarded by the National Institutes of Health.

BACKGROUND OF THE INVENTION

1. Field of Invention

The present invention concerns a simple, robust and precise instrument for constructing tissue arrays. The instrument may be operated manually or automatically.

2. Discussion of the Related Art

Some cancer patients respond well to a particular cancer therapy or combination of therapies. Others do not, but may respond to a different treatment. Scientists at the National Human Genome Research Institute (NHGRI) at the National Institutes of Health (NIH), in collaboration with the University of Tampere in Finland and the University of Basel in Switzerland, are developing a new research tool, which they call the "tissue chip," that they expect will eventually help them learn how to distinguish among subgroups of cancer patients and eventually predict which subgroups will respond to specific therapies. The tissue chip technology, they believe, will also help illuminate the process of cancer development. Such detailed new information can then be used to identify critical molecules for development of cancer therapies.

The tissue chip is a thin section of a tissue microarray that permits massive parallel processing of biological samples, making it possible for researchers to simultaneously compare a variety of molecular markers—DNA, RNA, and protein—in cancer tissues from hundreds or thousands of patients. As many as 1,000 tissue biopsies from individual tumors can be studied in a single tumor tissue microarray. The tissue chip thus makes it possible to simultaneously test thousands of patient tissue specimens which pathology laboratories have traditionally analyzed one specimen at a time. The power of this technology is expected to accelerate numerous areas of research, including testing of newly isolated genes to determine if they may be of clinical utility as molecular cancer markers.

In a study of breast cancer tissue microarrays (Kononen et al "Tissue microarrays for high-throughput molecular profiling of tumor specimens", Nature Medicine Vol. 4, Number 7 July 1998 pp. 844–847) researchers analyzed six gene amplifications and expression of the p53 and estrogen receptor genes believed to play a role in breast cancer. These researchers used genotyping in the search for cancer susceptibility loci, comparative genomic hybridization (CGH) for copy number alterations, as well as cDNA microarray technology for gene expression surveys, and recently discovered amplification of a steroid receptor co-activator, AIB1, in breast cancers as well as amplification of the androgen receptor (AR) gene in recurrent, hormone-refractory prostate cancers.

Each microarray is a block which may be comprised of 1,000 individual cylindrical tissue biopsies or "cores". Each microarray can be sliced into 200 consecutive sections of 5 micrometers each by traditional means (i.e., microtomes, etc.). The result is multiple nearly identical sections (tissue chips), each of which is used to make one ordinary microscope slide. With each of the cores then being represented as a minuscule dot in the same position in the matrix on each of the 200 microscope slides, it became possible to quickly analyze hundreds of molecular markers in the same set of specimens. Sections of the microarray provide targets for parallel in situ detection of DNA, RNA and protein targets in each specimen on the array, and consecutive sections allow the rapid analysis of hundreds of molecular markers in the same set of specimens. In the Kononen et al study, the tissue chip made it possible to complete in about one week what traditional methods would have taken from 65 to 12-months.

The tissue chip is also expected to be particularly useful in analyzing the thousands of tumor tissue samples stored in pathology labs all over the world. Previously, it would not have been considered practical to analyze these thousands of archived tumor tissue samples for hundreds of molecular markers—one at a time. Now, with the tissue chip, pathologists can take their existing archives, turn them into tumor arrays, and analyze an entire archive with just a few experiments. Pathologists can also array archived tissue samples from clinical trials of existing cancer drugs, and look for markers—a gene expression pattern or set of genetic changes in the tissue—associated with whether or not a specific participant in the trial responded to the therapy.

While tissue chips may significantly accelerate the assaying process, it has created a new challenge—a considerable investment in time and labor is necessary to manually extract samples from donor tissue and to assemble these specimens into a tissue array (Battifora, H., "The multitumor (sausage) tissue block: novel method for immunohistochemical antibody testing", Laboratory Investigation Vol. 55, pp. 244–248, 1986).

U.S. Pat. No. 4,820,504 entitled "Multi-specimen tissue blocks and slides" (Battifora) teaches a method of preparing a multi-specimen tissue block, and sections thereof, comprising forming a plurality of different antigenically reactive tissue specimens into rods having a relatively small cross-sectional area and a relatively great length, bundling the rods in a substantially parallel relationship on a casing, wrapping the rods in the casing, embedding the wrapped rods in an embedding medium to form a tissue block in which the rods are perpendicular to the face of the block, and dividing the block into sections which each contain a cross-section of each of the rods. While many specimens could be located in a compact area, it became difficult or impossible to track the identity of the various specimens.

U.S. Pat. No. 5,002,377 entitled "Multi-specimen slides for immunohistologic procedures" (Battifora) addresses this identity problem and teaches a process for producing a slide bearing a spaced array of specimen fragments which comprises (i) cutting at least one specimen into a plurality of narrow strips; (ii) separating the plurality into groups of specimen strips; (iii) separately positioning strips from the groups in parallel grooves in a mold; (iv) embedding the strips in the mold in a first embedding medium to provide a structure comprising a base member having opposed first and second surfaces, the first surface being substantially planar; the second surface having ridges containing a specimen strip extending therefrom; (v) forming a stack of elements, each element corresponding to the structure, with the terminal surface of the ridges of an upper structure abutting the substantially planar first surface of the next lower structure; the spaces between the ridges defining channels for receipt of a fluid; (vi) embedding the stack in a second embedding medium to form a block having a spaced array of parallel specimen strips embedded therein; the strips being so arranged that a section of the block includes a spaced array of cross-sections of each of the embedded specimen strips; (vii) dividing the block into sections each containing a spaced array of cross-sections of each of the embedded specimen strips; (viii) mounting at least one of such block sections on a slide. While this method forms tissue samples into a grid pattern in which it is possible to track the identities of individual samples, the method is time consuming. Further, the method is not suitable for assembling into a single array hundreds of core samples from hundreds of individual donors.

More recently a technique has been developed wherein biological tissue arrays are constructed simply as arrays (rows and columns) of cores of biological tissue, each core having been punched from an individual donor tissue sample and embedded at a specific grid coordinate location in a sectionable block typically made of the same embedding material used for the donor tissue. The process of constructing micro-arrays involves two hollow needle-like punches. One, the "recipient punch", is slightly smaller and is used to create a hole in a recipient block, typically paraffin or other embedding medium. The other, the "donor punch", is larger and is used to obtain a core sample from a donor block of embedded biological tissue of interest. The punches are sized such that the sample obtained from the donor block (and corresponding to the inner diameter of the donor punch) just fits in the hole created in the recipient block (and corresponding to the external diameter of the recipient punch). Thus the sample snugly fits in the recipient block, and a precise array can be created. Either the donor or recipient block may be removed and be replaced, as desired, by one or more other donor or recipient blocks during the process to create a multi-specimen array. Micrometer drives or other precision linear positioning means are used to position the punch assembly with respect to the recipient block or the recipient block with respect to the punch assembly.

While it is possible, with time, patience, and skill, to create the above described tissue array using the instruments presently available, there is a clear need for improvement. Using slides and drive mechanisms to first move the recipient punch into position and alternatively, the donor punch, is cumbersome, expensive, slow and prone to misalignment errors. It is clearly desirable that the donor punch reach exactly the same position that the recipient punch reaches on the recipient block for a given setting of the micrometer drives. If it does not, the sample retrieved from the donor block will not pass smoothly into the hole just created for it in the recipient block, but instead will be damaged or lost.

The manual methods have largely been superceded by those aided by instruments in view of the speed, precision and increased pattern density of the latter. At least one semiautomatic system has been proposed but not realized. This semiautomatic system includes a punch platform mounted to move up and down (z-axis). A stylet and stylet drive are located centrally on the punch platform. On one side of the stylet there is provided an inclined recipient punch drive comprising a reciprocating ram that carries a tubular recipient punch at its distal end. On the other side of the stylet there is provided an inclined donor punch drive comprising a reciprocating ram that carries a tubular donor punch at its distal end.

To operate, first a tissue array block is placed below the punch platform, the recipient punch is extended until the recipient punch is below the stylet, and the punch platform (including the extended recipient punch, the retracted stylet, and the retracted donor punch) is lowered to cut a recipient core into the paraffin tissue array block. The punch platform is raised, a discard container is placed below the extended recipient punch, and the stylet is extended downwards into the recipient punch to expel the paraffin from the bore. The stylet is then retracted, and then the recipient punch is retracted. Next, a donor block is placed below the punch apparatus and the donor punch is extended until it occupies the space previously occupied by the recipient punch. The punch apparatus is lowered and the donor punch cuts a core sample from the donor block. The punch apparatus is then raised, and the recipient block is placed below the punch apparatus. The punch apparatus is lowered until the donor punch is located over the empty recipient hole, and the stylet is extended into the donor punch to expel the core sample into the recipient hole. The procedure is continued hundreds of times to form a tissue array block.

However, a number of disadvantages are associated with this apparatus. First, since there is only one stylet, and since the outer diameter of the stylet is dimensioned to fit snuggly within the inner diameter of the punch, it is only possible to use two punches having the same internal (and thus external), diameters in this instrument. Since needle-like donor and recipient punches are usually of different sizes, this instrument is not suitable for making micro-arrays. Second, considering that the steps for drilling and planting each core may have to be repeated 1,000 times to make a tissue array, and considering that each step introduces the possibility of operator error, there is a need to reduce the number of steps. Third, the fact that a single stylet is associated with two different punches makes it imperative that the punches, when extended, are positioned precisely below the stylet, as well as precisely above the target position on the donor or recipient block. The fact that the punches, when under the stylet, are in their fully extended position, means that the punches are in their structurally weakest position, and further, considering that any play or misalignment is amplified by the length of extension, any imprecision in positioning is magnified. Any misalignment of the punch could result in damage to the stylet and/or prevent proper planting of the donor core sample in the recipient block. Yet another deficiency is the inability to adjust the positioning of the punches with respect to the stylet. Further yet, this apparatus requires three actuator means—one for extending and retracting the stylet, one for the recipient punch, and one for the donor punch. As the number of moving parts increases, so does the likelihood of equipment failure. Finally, operation of the punch is not ergonomically or intuitively logical, thus increasing the likelihood of operator errors.

It is thus an object of the invention to provide an apparatus with which the precise sequential positioning of multiple punches can be effected reliably and inexpensively. It is a further object that this punch positioning as well as the punch stroke motion be easy to actuate by hand in a manually operated instrument. It is a further object of the invention to provide an instrument for the semi-automatic or automatic production of tissue arrays.

It is a further object of the present invention to overcome the cumbersome quality and imprecision of the prior art and to provide a simple and precise means of alternately positioning the two needle-like punches in a tissue micro-array constructing instrument.

SUMMARY OF THE INVENTION

The inventor analyzed the steps involved in the construction of a tissue array and the deficiencies of the prior art devices, and following a series of prototyping experiments developed an instrument that overcomes the above-described deficiencies.

The invention thus concerns a simple and robust yet precise instrument for constructing tissue arrays. The instrument may be operated manually or automatically.

The instrument comprises:

a punch platform carriage displaceable in the Z axis;

a punch platform mounted on said punch platform carriage and displaceable between at least first and second positions with respect to said punch platform carriage, said positions precisely defined by détentes;

at least first and second punch units mounted on said punch platform, each punch unit comprising a punch and a cooperating stylet;

means for holding a recipient block;

means for selectively repositioning said recipient block and punch platform in X and Y axis with respect to each other;

means for guiding the movement of at least one of said recipient block and punch platform carriage in the Z axis relative to each other;

wherein said first punch unit comprises a recipient punch and associated stylet and said second punch unit comprises a donor punch and associated stylet, said donor punch having an internal diameter corresponding to the external diameter of the recipient punch, wherein when said punch platform is in said first position said recipient punch is in position over said recipient block holder and in alignment with said Z axis, and when said punch platform is in said second position said donor punch is in position over said recipient block holder and in alignment with said Z axis.

The punch platform can be mounted on the punch platform carriage in any of a number of ways to be displaceable between at least first and second positions with respect to said punch platform carriage. For example, the punch platform may be pivotable about a horizontal (X-) axis, with the punches extending radially out from the axis of rotation (turret style). Alternatively, the punch platform may pivot or revolve around a vertical (Z-) axis, with the punches parallel to the axis of rotation (revolver style). Further, the axis of the punch platform may be at an intermediate angle (e.g., 45 or 60 degrees from the X, Y or Z axis, like a turret lathe. Further yet, the punches may be displaceable linearly along a horizontal guide (slide style). Finally, the displacement of the punches may also be along a curved guide, thus combining some of the features of the turret style and the slide style.

The important feature is that mechanical détentes or stops are provided which mechanically arrest the movement of the platform in precisely defined positions. This greatly saves in time and improves in accuracy over use of conventional precision linear positioning means. By the simple step of moving the punch platform from the first position to the second position, or vice versa, the positions precisely defined by détentes or stops, either punch can be quickly moved into position either manually or by automatic means, making it possible to quickly alternate from one punch to the other.

The instrument may be provided with means for adjusting the limits of travel of the punch platform with respect to any of the détentes or stops.

It is of course also not necessary that the axis of rotation or sliding be in the X, Y or Z axis; it is merely necessary that one punch be displaced with respect to the other, and that the punch in the operating position be aligned in the punching (Z-) axis. The bearing or slide and associated end-stops or détentes defining the path and limits of motion of the punch platform are of a quality to prevent any wobble or motion other than that desired and to ensure that the two punches will alternatively occupy exactly the same position.

The means for selectively repositioning said recipient block and punch platform in X and Y axis with respect to each other may be slides and drive mechanisms, or micrometer drives.

A removable bridge may be used for supporting the donor blocks over the recipient blocks or vice-versa. This makes it possible to keep the recipient block in registry and minimizes the need to reposition blocks using the X and Y positioning means.

The instrument may be fully manually operated, semi-automated or automated, and be provided with means such as an electromagnetic actuator means or hydraulic or pneumatic cylinder to pivot said member between said first and second positions.

The rest of the instrument employing the improvement which constitutes the present invention may be similar to that already described in the prior art. For example, micrometer drives or the like may be used to position the punching mechanism in the X and Y directions with respect to blocks, or the blocks with respect to the punching platform.

It is possible and often desirable to provide a spring arranged in a toggle configuration to hold the pivoting member firmly at one end of the travel or the other. Thus, one of the punches may be held securely in the first position by said spring, yet reasonable manual or powered force can cause the pivot means to pivot to the second position. Small forces, for example such as may be inadvertently exerted by the operator while controlling the punching motion, will not change the lateral punch position. Alternatively, spring or gravity means may be provided for biasing the pivoting platform towards only one of said first and second end positions, with actuation of an electrical, pneumatic or hydraulic actuator overriding the spring force and driving the pivoting platform towards the alternate position.

The present invention thus provides a means for holding the recipient or donor block very firmly and precisely while allowing the operator to easily remove the block and reposition it or another one. One or more magnets permanently fixed to a base plate and provided with lateral positioning stops or curbs, also affixed to the base plate, provide this function by attracting a ferromagnetic plate fixed to the bottom of the recipient block holder.

The instrument according to the present invention is simple, precise and easy to adjust, align and use.

BRIEF DESCRIPTION OF THE DRAWINGS

The present invention has the above as well as other objects, features and advantages which will become more clearly apparent in connection with the following detailed description of a preferred embodiment, taken in conjunction with the appended drawings in which:

FIGS. 2a–2e show the recipient punch sequencing through the steps of forming a cylindrical hole in the recipient block.

DETAILED DESCRIPTION OF THE INVENTION

Figure 1:
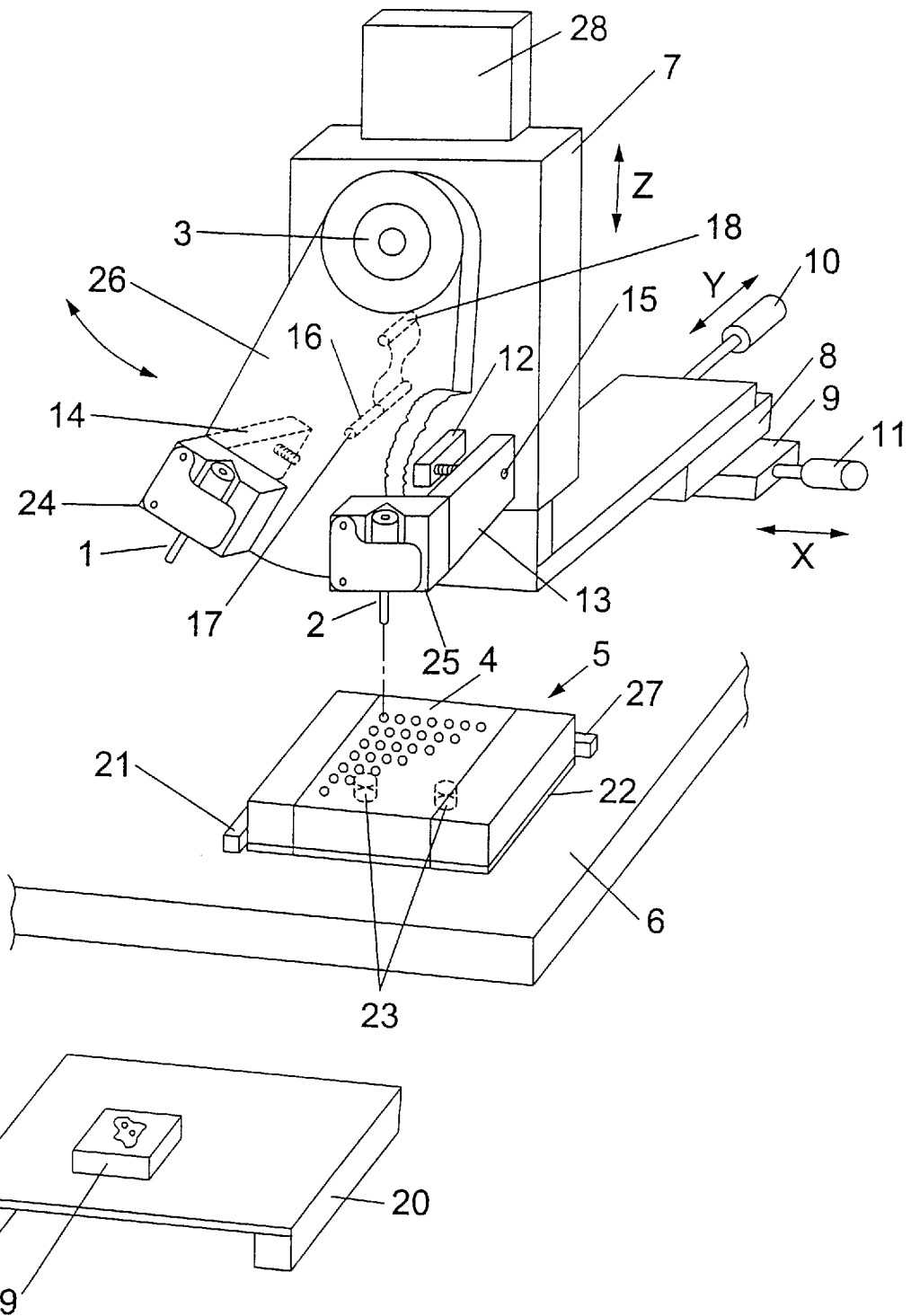
FIG. 1 is an elevated perspective view of an isometric partial cutaway drawing of a first (pivot type) embodiment of the inventive instrument, seen from the operator's perspective.

The invention provides a simple, robust and precise instrument for constructing tissue arrays. Employment of the instrument reduces the time, labor and complexity of assembling hundreds of specimens into regular arrays of cores of embedded biological tissue in a sectionable block.

Arrays are constructed by taking samples from a series of donor tissues, one at a time, using a hollow, preferably needlelike, donor punch and placing each sample sequentially in a recipient of complementary shape in a recipient material by a recipient punch, thereby forming an array of tissues in the recipient block. Each punch comprises a punch tube and an associated stylet guided within the punch tube. The stylet has an outer diameter approximating that of the donor punch inner diameter, and is dimensioned for sliding within the punch tube. The process of forming a hole in a recipient material such as paraffin, taking a sample of tissue from a donor specimen, and planting this sample in the hole in the recipient material, is repeated until a tissue array is formed comprising hundreds of tissue samples arranged in assigned locations in the recipient material.

The sample punched from the donor tissue sample is preferably cylindrical, about 1–8 mm in length, with a diameter of from about 0.4 to 4.0 mm, preferably about 0.3–2.0 mm. The recipient punch is slightly smaller than the donor punch and is used to create a hole in a recipient block, typically made of paraffin or other embedding medium. The punches are sized such that the sample obtained from the donor block just fits in the hole created in the recipient block. Thus the sample snugly fits in the recipient block and a precise array can be created.

The donor and/or recipient blocks may be alternately removed and replaced in an appropriate holder during the process, or one or both of the donor and recipient blocks may be held in place in designated donor and recipient holders, one of which being displaceable from the punch operating position, such as by pivoting the holder about a vertical axis. Further, donor or recipient blocks may be removed and be alternated with one or more other donor or recipient blocks to create more than one array from one set of donor blocks. Further, the holder(s) may be designed to hold two or more donor or recipient blocks, or other elements such as recipients or waste bins for cores removed from the recipient block in forming the recipients.

The appropriate point at which to punch the donor block can be determined in any conventional way. For example, a section of the donor block (presumed representative of the tissue imbedded in the entire donor block) can be mounted on a slide, inspected under a microscope, and target sites can be plotted and recorded, for example, in a computer. Then, an available target site can be selected and the donor block punched at the selected site either by manual adjustment of the micrometer drives, or by feeding the coordinates to a CNC controlled X-, Y-positioning means. Alternatively, the slide made from the donor block could be stained to reveal structures of interest if necessary, and be superposed over the donor block, and the donor punch be aligned over the target site. Then, the slide can be removed, and the donor punch brought down to punch the donor block in the selected position.

Micrometer drives or other precision linear positioning means may be used to reposition the punch assembly at regular increments from one position to the next adjacent position with respect to the recipient block matrix or array, or to reposition the recipient block and/or donor block with respect to the punch assembly.

It is clearly desirable that the donor punch reach exactly the same position that the recipient punch reaches on the recipient block for a given setting of the micrometer drives. It is further desirable that this motion be easy to actuate by hand in a manually operated instrument. This is achieved by providing at least first and second punch units on a punch platform mounted on a punch platform carriage and displaceable between at least first and second positions with respect to said punch platform carriage, said positions precisely defined by détentes or stops. In a first embodiment of the invention the punches are donor and recipient punches mounted on a horizontal or vertically pivotable arm such that when the pivotable member is in a first position the recipient punch is in position for punching by moving the pivotable arm towards the block being operated on, and when the pivotable member is in the second position donor punch is in position for punching by moving the arm towards the block being operated on. In a second embodiment of the invention the punch platform is mounted on a horizontal slide. In each case the punches are alternately positionable over the donor or recipient blocks for punching bore holes by relative movement between the punch and blocks (i.e., either the punches are moveable relative to the blocks, or the blocks relative to the punches).

In accordance with the present invention at least two punches—one donor punch and one recipient punch—are employed; however, it is possible to employ three or more punches as desired. For example, it is possible to provide three punches, where the first punch has the smallest diameter and serves as the receptacle punch with respect to the second punch of intermediate diameter, which serves as the donor punch for the first punch. The third punch has the largest diameter and serves as the donor punch with respect to the second punch of intermediate diameter, which serves as the receptacle punch to the third punch. This permits the operator to select the gauge of punch best suited for a particular donor tissue morphology.

Each punch is provided with its own stylet for clearing material within the punch. Each stylet has an outer diameter approximating that of the inner diameter of the punch with which it is associated, but is slightly smaller than the inner diameter of the punch so as to be slidably guided within the punch. The stylet can be manually operated or powered by mechanical (e.g., wind-up), electrical, electromagnetic, pneumatic or hydraulic means. The punches are preferably circular in cross-section, but may be any shape, such as oval, square, rectangular, etc. It is also possible to form the stylet of a metal such as surgical steel, of plastic such as teflon coated polyvinyl chloride, or of a rubber material. The stylet could also be made of uniform cross section, or as a piston and piston rod design, or a ribbed design, etc. It may even be possible to form the stylet as a balloon. The function of the stylet may even be filled by a fluid medium such as air, oil, or water pumped to eject the recipient cores and/or donor samples, with no solid stylet.

A further embodiment of the instrument of the invention makes it possible to allow donor blocks to be placed in a donor block holder in position for removal of sample cores, without having to remove the recipient block from a recipient block holder. This is achieved in the present invention by providing, for example, a bridge plate that can be positioned just above the recipient block and resting on the base plate. This bridge is easily removed each time it is necessary to access the recipient block and put in place to hold donor blocks. A displacement of the pivotable arm in the X or Y direction thus achieves a displacement of the punch operating position over both the donor and recipient blocks. Since the donor and recipient blocks are maintained in place in their respective holders, and only one holder is pivoted into and out of place, it is virtually guaranteed that the punches remain in registry over the donor or recipient position, thus ensuring fast, easy, and properly positioned operation.

The present invention will now be described in detail by reference to the figures. Elements which are identical in the first and second embodiments will be designated with the same reference numbers.

FIG. 1 shows in semi-schematic form the various features of the instrument according to a first embodiment of the invention. In the illustrated embodiment, recipient punch 1 is smaller and is used for making holes in the recipient block 4. Donor punch 2 is larger, having an inner diameter corresponding to the outer diameter of the recipient punch 1. Donor punch 2 is used for obtaining the core samples from the donor block 19 and planting them in the holes formed by recipient punch 1 in the recipient block 4. Blocks with recesses 24, 25 and clips 41 (FIG. 3) are used for holding the respective punches on the pivot arm 26. Pivot arm 26 is pivotably mounted on vertical carriage or slide 7 by pivot bearing 3. Slide 7 moves vertically (Z axis) on rail 28 which moves front to back (Y axis) on horizontal slide 8 controlled by drive 10. Slide 8 moves laterally (X axis) on slide 9 controlled by drive 11. Slide 9 is affixed to a base plate 6.

Also fixed to base 6 are magnets 23 which hold ferromagnetic plate 22 against the base plate and against curbs or stops 21 and 27. Ferromagnetic plate 22 is part of recipient block holder 5 which holds recipient block 4. Multiple holes or samples can be seen arranged in an X-Y grid pattern or matrix in block 4. Thus, the holder 5, including the plate 22 and containing the block 4 can be easily removed and reinserted to the same position on base 6, but is firmly held while in place.

Block 4 is formed of paraffin or a like material. Individual recipient holes can be punched onto the block either immediately prior to cutting and planting the donor sample, or an entire grid pattern of recipient holes may be cored into the recipient block prior to harvesting samples from the donor block. However, due to the amorphous nature of the waxy donor block, it is preferred to punch the recipient holes immediately prior to transplanting donor samples, in order to ensure the highest possible degree of alignment.

In the illustrated embodiment spacer bars 13 and 14 are permanently affixed to pivot arm 26. Each spacer bar is provided with an adjustment screw 15, each screw contacting an opposite side of the same stop 12, stop 12 being fixed with respect to the slide 7, thus limiting the pivot movement and defining when the pivot arm is in either the first or second position. The adjustment screws allow the exact end of the travel to be set precisely. Thus, at one end of travel donor punch 2 is positioned in registry over a specific hole in the recipient block (as drawn). At the other end of the travel, recipient punch 1 is precisely over the same location, as long as X and Y axis drivers 10 and 11 have not been actuated.

The pivot arm may be spring biased towards one of the two end positions, such that energization or application of an overriding opposite force is all that is needed to pivot the arm to the alternate position, and deactivation or cessation of application of force is all that is needed to pivot the pivot arm back to the start position. Alternatively, the spring can be a toggle spring, such that upon manual pivoting of the pivot arm from the first position to the second position or from the second position to the first position, the pivot arm remains in the end position in which it is placed. In the illustrated embodiment, pin 17 protrudes from the back of arm 26 and pin 18 protrudes from the front of slide 7. Toggle spring 16, a compression spring, connects the two pins. This spring has maximum stored energy when the pivot arm is in the middle of its travel, and minimum when the arm is at either end of its travel. Thus, except when external manual pressure is exerted to change punch positions, the arm is held against one of the two stopped positions. Of course, any of the various means can be used to bias the pivot arm toward the end position, e.g., gravity, torsion springs, etc.

In the illustrated embodiment, donor tissue block 19 rests on removable bridge 20 that can be seated or freely moveable straddling recipient block holder 22. It is apparent that the donor block could also be provided on a horizontally pivotable arm, preferably an arm with two pivot joints, such that any point on the donor block could be positioned below the donor punch.

Although there are many ways to construct a device within the spirit of the invention, the principle of operation would remain the same, and the operation of the embodiment which is illustrated in FIGS. 1 and 2, wherein pivoting is accomplished manually and wherein core punching is automated, will now be described in greater detail. The process of punching the recipient block will be the same as the process for punching the donor block. Thus, only the process of punching the recipient block will be discussed in detail.

The specimen transfer cycle begins when the operator positions the recipient punch in position over the recipient block and moves the recipient punch vertically downward into the recipient block to make a bore hole. Boring begins as the tip of the punch touches the surface of the block. In a manual process, this contacting is detected by vision and touch. In a semi-automatic or automatic tissue array instrument, the computer or other control system must be able to detect the surface of the blocks (especially the donor blocks). These blocks may come from many different sources, including recently made blocks and archival blocks, as well as blocks from many different laboratories or clinics. Thus the height of these blocks may vary widely. Even recipient blocks all made at the same time in the same laboratory may vary in height due to the vagaries of the paraffin material, the molds, and the cooling process.

Figure 4:
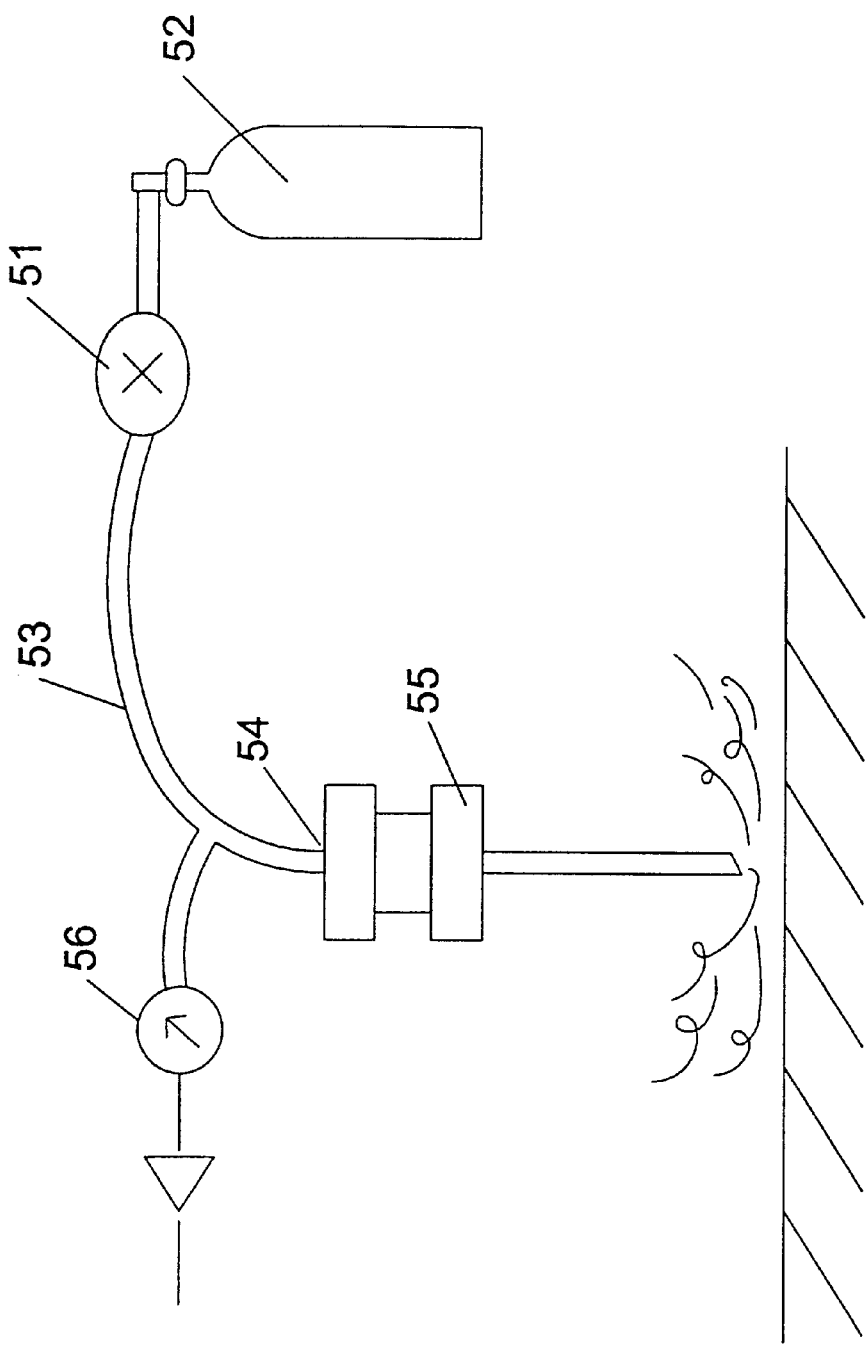
FIG. 4 is a side partially schematic representation of a system wherein the solid stylus is replaced by pneumatics.

Of course, in the case that the function of the stylet is not performed by a solid ram but is instead performed by a fluid medium such as air, oil or water, surface sensing would be different from the above, for example, using back pressure to sense when the punch is empty but close to the surface. This works well, especially with air, since leaks would not be a problem and it is rugged and simple and would stop "pushing" once the core or sample were clear of the punch. There would simply be, for example, a valved 51 compressed air supply 52 connected via air hose 53 to the top 54 of either or both punches 55, with a pressure sensor 56 in fluid communication with the air hose 53 near the punch (FIG. 4).

As shown in FIG. 2a, prior to contacting recipient block 30, recipient punch 2 is positioned over the target site of the recipient block. Since it is desired in the operation of the instrument to penetrate to a fixed depth or distance from the top surface of the block, and since that surface may vary in height from block to block and even within the top surface of an individual irregular block, the instrument must move the punch down the desired distance measured from the top surface at the locus of interest. The instrument must thus be capable of detecting the block top surface.

The instrumentation art has proposed various optical surface detection systems such as laser diode triangulation devices (e.g. Dynavision Inc. model SPR-02, and several others), or structured light patterns visualized by an operator (e.g. Coherent-Ealing catalog #31-0458). Both are expensive as well as bulky. Both also suffer from imprecision, since the surface in question in the present invention may be paraffin or similar waxy compounds which are highly translucent. Thus, since the light is reflected and scattered from several different heights within the paraffin and embedded tissue, it is difficult to get an accurate indication of the actual surface using these optical systems. In addition, the structured light systems require human operator intervention which obviously impairs the desired automatic operation.

The present invention solves this problem in a simple manner and uses the stylet 32 which is already present within the punch tube 31 as the probe to sense the surface of the block. The stylet is manufactured to protrude a fixed and known distance from the bottom of the punch tube when the punch tube is empty of donor or recipient material and the stylet has extended all the way to the bottom of the punch. Thus, as the punch is brought down to the block, the stylet will be the first element to touch the block as shown in FIG. 2b. The stylet is free-floating at this stage (i.e., stepper motor if employed is inactivated) in the cycle, thus it will not penetrate into the block 30 as the punch tube 31 is brought further down. The stylet tip will remain resting on the surface of the block but the punch will continue to move downward relative to the block and relative to the stylet. This is the same as saying that the stylet will move up with respect to the punch tube. This relative motion can be detected in a number of simple, precise and robust ways, giving rise to a signal which is routed to a computer or other control means (not shown). The control means can then record the signal corresponding to the current position of the punch, and thus records the position of the surface of the block.

Although optical, electromagnetic or other means could be used to detect this motion, a simple electrical discontinuity circuit has proven most useful, robust and simple, as well as extremely inexpensive and requiring practically no space in an otherwise crowded region of the instrument. For example, as shown in FIGS. 2a–2e, the hub of the stylet 32 (not shown in FIG. 1) and the punch tube 31 are typically made of an electrically conductive material such as brass. Stylet and punch tube are provided, at or near their upper ends, with radial flanges or collars 34 and 33, respectively. Electrical insulation 35, such as a plastic or rubber sleeve, may be provided between stylet 32 and stylet flange 34. The punch tube 32 is grounded via the clamp that is holding it, and the stylet flange 34 is attached to a flexible wire. Of course, the stylet flange could be grounded, and the punch be connected to current. When the stylet is at the lowermost position of travel with respect to the punch tube, the punch and stylet flanges 33, 34 are in electrical contact as shown in FIG. 2a. As soon as the stylet 34 contacts the block surface during a downward movement of the punch, this flange-to-flange electrical contact is broken and a signal is sent (or interrupted) to the controller, as shown in FIG. 2b. Computer or controller (not shown) registers the surface position at this locus on the array, and provides control signals to continue moving the punch downwards for a predetermined distance until punch tube 31 has penetrated the desired distance into block 30, as shown in FIG. 2c. As material from the block enters the punch tube, the stylet and stylet flange, which are free floating, continue to move upwards relative to the punch tube.

The punch tube 31 having penetrated the desired distance into the block 30, the controller sends a signal to raise the punch (i.e., to raise the vertical carriage or slide 7, including pivot bearing 3, pivot arm 26, and the punches 1, 2 mounted on the pivot arm 26). Since the material inside the punch tube will break free of the block 30 and remain in the tube, the recipient block will exhibit a cylindrical hole 36 after the punch tube has been extracted. If desired, in order to facilitate the breaking-free of the core material from the block prior to raising the punch, toggle bar 39 is provided, which can be moved back and forth to ensure complete breaking free of the core material.

Next, either a waste tray is placed below the raised recipient punch, or the recipient punch is pivoted out to the inactive position at which time the recipient punch tip is positioned over a waste tray, and the controller sends a signal to cause the stylet to return to the start position with stylet tip protruding from the end of the recipient punch tube. As the stylet moves back to the starting position, the stylet expels any material from within the recipient punch tube. Contact of the stylet and punch tube flanges 34, 33 sends a signal to the controller that the stylet has successfully returned to the start position and is ready for use. Failure of the stylet to return to the start position can generate a failure signal and/or alarm and cause automatic interruption of the array construction process. Obviously, in view of the ease of pushing stylet flange 34 downwards manually, this part of the operation could be conducted manually if desired.

As discussed above, besides the recipient punch 2, a donor punch 1 is provided on the pivot arm 26. Manual or automatic pivoting of the pivot arm about a horizontal axis from one end position to the other end position is all that is necessary to bring about a precisely aligned change of punches, in this case, a replacement of the recipient punch with the donor punch. End stop 12 and a toggle spring 16 allow either punch to be manually swung into position parallel to the vertical slide axis or (Z axis) and retained there.

The donor punch 1 is similar in construction to the recipient punch, except that the inner diameter of the donor punch tube is dimensioned to correspond to the outer diameter of the recipient punch tube.

Next, a donor block 19 is brought into place below the donor punch 1. This can be done by removing recipient block 4 from holder 5 and replacing it with donor block 19. Alternatively, donor block can be provided on a two-pivot horizontal swingarm, such that any point in the block can be easily positioned under the donor punch. For ease of operation and simplicity of manufacture, the donor block can simply be provided on a bridge 20 designed to fit over the recipient block. While precise positioning of the donor block may not be necessary, it is possible in a simple manner by simply aligning bridge supports with the curbs or stops 21 and 27 of the holder 5. The removable bridge is put in position, with a donor block placed on top of it. With the donor block precisely in place, a signal is sent to the controller, which next sends a signal to lower slide 7, including donor punch 1.

The donor punch is employed to remove a core tissue sample from the donor block in the same manner that the recipient punch removed a core of material from the recipient block. A vertical motion of the punch relative to the donor block (i.e., a lowering of the punch or a raising of the donor block, followed by the reverse motion) is used to obtain a sample core from a region of interest in the donor block, with control of the process being the same as discussed above for the recipient punch.

Next, the bridge and donor block are removed, and the donor punch is moved vertically downward to just above the hole in the recipient block, the position of the recipient block surface having been measured and recorded as part of the step of recipient block core hole formation. At this point the stylet is used to expel the core sample from the donor punch tube into the cylindrical hole in the recipient block. Since there has been no removal and replacement of the recipient block, the precise positioning of the recipient block is assured.

In this manner, one cycle of the process of forming the tissue array has been completed. The next cycle begins once the punch is relocated relative to the recipient block. Manual micrometer drives allow fine repositioning of the pivot arm, and thus punches, in the X and Y axis with respect to the recipient block held removably on a base by magnets. Once the lateral position has been incrementally changed to the next position with drives 10 and or 11, the cycle is repeated.

Any sequence of donor block substitutions or recipient block substitutions can be made, resulting in any desired composition of tissue array. It is possible to provide an elongated tray for positioning multiple donor or recipient blocks.

Computer programs or controllers for controlling the positioning and actuation of instruments are well known and need not be described in detail herein. Reference may be made to U.S. Pat. No. 4,979,093 (Laine et al) entitled "XYZ Positioner"; U.S. Pat. No. 3,665,148 (Yasenchak et al) entitled "Six-Axis Manipulator"; U.S. Pat. No. 5,355,304 DeMoranville et al) entitled "Clinical Laboratory Work-Flow System which Semi-Automates Validated Immunoassay and Electrophoresis Protocols"; U.S. Pat. No. 4,484,293 (Minucciani et al) entitled "Dimensional Measurement System Served by a Pleurality of Operating Arms and Controlled by a Computer System"; and U.S. Pat. Nos. 5,567,715 5,355,439 (Bernstein) entitled "Method and Apparatus for Automated Tissue Assay".

Once the desired number of tissue samples have been transplanted from the donor block(s) to the recipient block, the "tissue chips" can be formed by slicing the tissue array block into hundreds of consecutive thin sections of, e.g., 5 micrometers in thickness, by traditional means (i.e., microtomes such as Model Cut 4055™ by Olympus Corp. of Tokyo, Japan, etc.; see, e.g., U.S. Pat. Nos. 664,118; 2,292, 973; 2,680,992; 3,420,130; 3,440,913; 3,496,819; 3,799, 029; and 3,975,977) to create multiple nearly identical sections, with each of the donor cores then being represented as minuscule dots on an ordinary glass microscope slide. Analyses that may be performed on the donor specimens include immunological analysis, nucleic acid hybridization, and clinicopathological characterization of the specimen.

Figure 3:
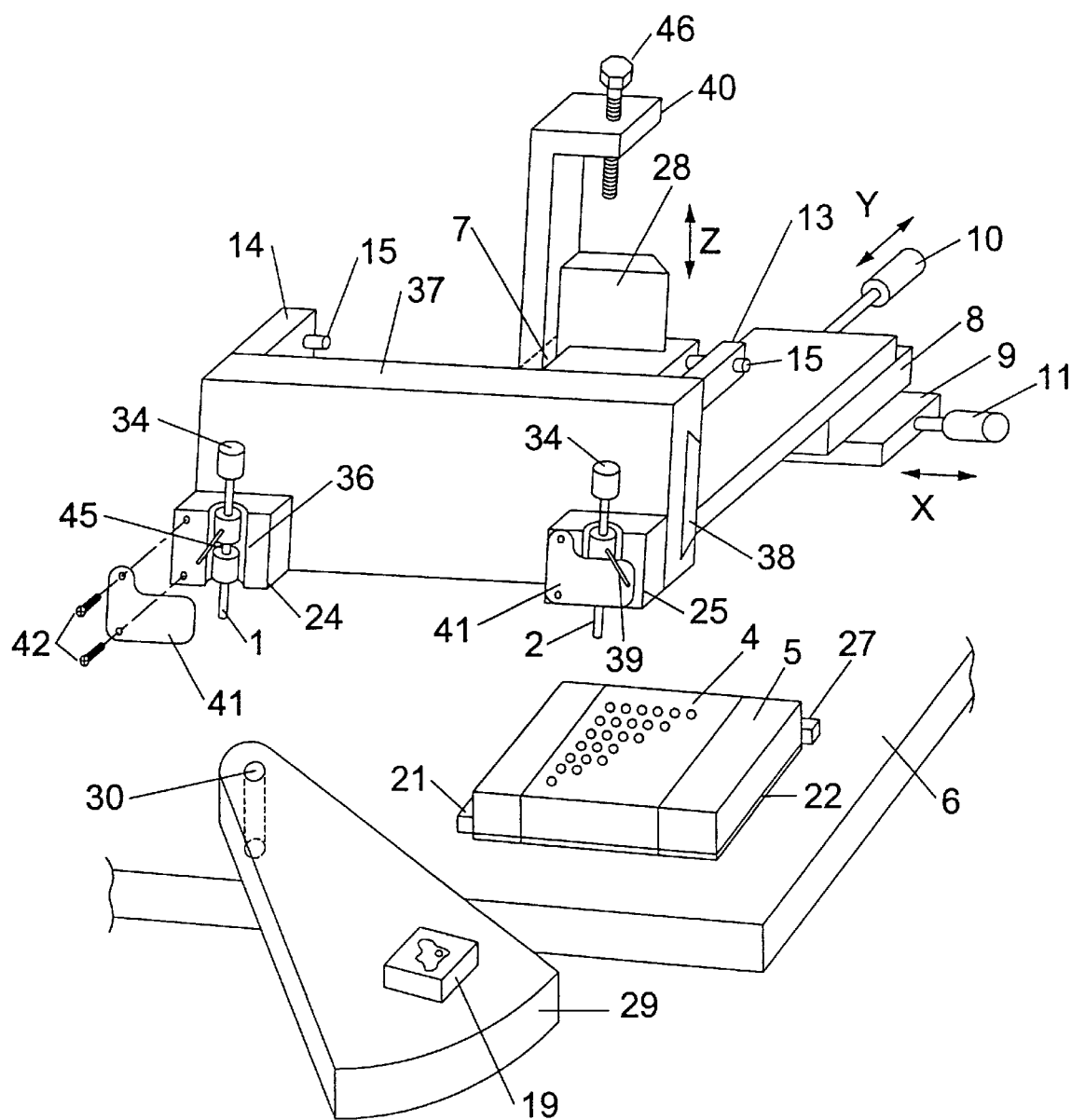
FIG. 3 is an elevated perspective view of a second (slide type) embodiment of the inventive instrument.

Next, an alternative embodiment of the invention as shown in FIG. 3 will be described, wherein the pivot arm mechanism used to reposition punches in FIG. 1 is replaced by a horizontal slide mechanism. A sliding punch platform 37 slides substantially horizontally on a slide 38 which is fixed to the vertical slide 7. Although this is shown as a motion in the X-axis, it could also be arranged in the Y-axis, or in any other substantially horizontal direction. The slide 7 provides the vertical punching motion as in the embodiment in FIG. 1. X and Y slides 8 and 9 and their respective drives 10 and 11 function as in FIG. 1, and slide 9 is attached to platform or base 6. Also, as in FIG. 1, recipient block 4 and associated components 5, 22, 21 and 27 are shown.

The sliding punch platform 37 slides to either side until either adjustment stop 15 in stop supports 13 and 14 contact part of the slide 7 or an attached part. Biasing or toggle springs may be used as in FIG. 1, and motion may be either manual or automated. Punch assemblies similar or the same as those in FIG. 1 are used, affixed at different lateral positions on plate 37. It should be noted that more than two punch assemblies may be attached to this plate. They may, for example, hold punch sets with different sizes or shapes for selection by the operator or controller.

Spring clips 41 are shown, one for each of the two punches. The clips are held with screws 42 and in turn hold the punches 1 and 2 in the v-blocks 24 and 25. The clip on punch 1 is shown in an exploded view and the clip on punch 2 is shown in place. Each punch has a circumferential groove 45 which engages a ridge, tab or pin (not shown) in the v-block, while allowing turning of the punch about is own axis. (There are many other ways of implementing this vertical location, such as circumferential ridge on the punch and a groove in the v-block, or using the top and bottom surfaces of the punch hub, etc.) Handles 39 attached to the punch hubs may be used by the operator to rotate the punches about their own axes to break the donor and recipient cores loose for removal from their respective blocks.

A depth stop screw 46 in an arm 40 attached to slider 7 may be adjusted to stop the vertical motion of slider 7 when the screw touches the ends of the slide 28. This depth adjustment is particularly useful for the manual punching of the recipient block, since the holes in this will normally all be of the same depth.

As an alternative embodiment of the bridge used for staging the donor block as shown in FIG. 1, a pivoting arm 29, attached to the platform 6 with a pivot 30 may be used to support the donor block(s). The pivot arm can be swung into position above the recipient block and holder, or out of the way. Of course, as discussed above, the block holder or this pivot arm could be moved in the Z axis relative to the punch similarly to the punch moving in the Z axis relative to a stationary block holder or pivot arm. A similar platform can be used to position a corresponding slide, or a slide can be positioned on a bridge above the donor block, to help visualize the donor block and select the target site.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

Now that the invention has been described,

What is claimed is:

1. An instrument for constructing arrays of tissue in a recipient block, the instrument comprising:
   a punch platform carriage displaceable in the Z axis;
   a punch platform mounted on said punch platform carriage and displaceable between at least first and second positions with respect to said punch platform carriage, said positions precisely defined by détentes or stops;
   at least first and second punch units mounted on said punch platform, each punch unit comprising a punch and a cooperating stylet;

means for holding said recipient block;

means for selectively repositioning said recipient block and punch platform in X and Y axis with respect to each other;

means for guiding the movement of at least one of said recipient block and punch platform carriage in the Z axis relative to each other;

wherein said first punch unit comprises a recipient punch and associated stylet and said second punch unit comprises a donor punch and associated stylet, said donor punch having an internal diameter greater than the recipient punch, wherein when said punch platform is in said first position said recipient punch is in position over said recipient block holder and in alignment with said Z axis, and when said punch platform is in said second position said donor punch is in position over said recipient block holder and in alignment with said Z axis.

2. An instrument as in claim 1, wherein said punch platform is pivotable about a horizontal (X-) axis between at least first and second positions with respect to said punch platform carriage, with the punches extending radially out from the axis of rotation.

3. An instrument as in claim 1, wherein said punch platform is pivotable about a vertical (Z-) axis between at least first and second positions with respect to said punch platform carriage, with the punches oriented parallel to the axis of rotation.

4. An instrument as in claim 1, wherein said punch platform is linearly displaceable along a horizontal guide between at least first and second positions with respect to said punch platform carriage.

5. An instrument as in claim 1, wherein said détentes or stops are mechanical détentes or stops.

6. An instrument as in claim 1, further comprising means for adjusting the limits of travel of the punch platform with respect to at least one of the détentes or stops.

7. An instrument as in claim 1, further comprising a removable bridge for supporting a donor block over the recipient block or vice-versa.

8. An instrument as in claim 1, wherein said stylet and punch have proximal and distal ends, the distal ends for contacting said blocks, when the distal end of said stylet when in the fully extended position extends beyond the distal end of said punch.

9. An instrument as in claim 8, further including a discontinuity circuit, wherein the electrical continuity of said circuit when said stylus is in the fully extended position is different than when said stylet is not in the fully extended position.

10. An instrument as in claim 1, further including electromagnetic, hydraulic or pneumatic actuator means for displacing said punch platform between said first and second positions.

11. An instrument as in claim 1, further including spring means arranged to hold the punch platform firmly against one or more of said détentes or stops.

12. An instrument as in claim 1, wherein at least three punches are mounted on said punch platform.

13. An instrument as in claim 2, wherein at least three punches are mounted on said punch platform.

14. An instrument as in claim 3, wherein at least three punches are mounted on said punch platform.

15. An instrument as in claim 4, wherein at least three punches are mounted on said punch platform.

16. An instrument as in claim 1, including means for holding multiple recipient blocks.

17. An instrument for constructing a tissue array, said instrument comprising:

means for positioning a first block of material;

a pivotable member pivotable between at least first position and a second position;

support means for selectively positioning said pivotable member in the X and Y axis relative to said means for positioning said block of material;

a recipient punch mounted on said pivoting member, said recipient punch including a recipient punch tube and a recipient stylet guided within said recipient punch tube, said recipient stylet having an outer diameter approximating that of the recipient punch tube inner diameter;

a donor punch mounted on said pivoting member, said donor punch including a donor punch tube and a donor stylet guided within said donor punch tube, said donor stylet having an outer diameter approximating that of the donor punch tube inner diameter;

wherein when said pivotable member is in said first position said recipient punch is in an operating position, and wherein when said pivotable member is in said second position said donor punch is in an operating position.

18. An instrument for constructing arrays of tissue in a recipient block, the instrument comprising:

a punch platform carriage displaceable in the Z axis;

a punch platform mounted on said punch platform carriage and displaceable between at least first and second positions with respect to said punch platform carriage, said positions precisely defined by détentes or stops;

a flexible hose;

at least first and second punches mounted on said punch platform, each punch having a hollow center channel in communication with said flexible hose;

fluid under pressure connected to said flexible hose via a valve;

pressure sensing means connected to said flexible hose;

means for holding said recipient block;

means for selectively repositioning said recipient block and punch platform in X and Y axis with respect to each other;

means for guiding the movement of at least one of said recipient block and punch platform carriage in the Z axis relative to each other;

wherein said donor punch having an internal diameter greater than the recipient punch, wherein when said punch platform is in said first position said recipient punch is in position over said recipient block holder and in alignment with said Z axis, and when said punch platform is in said second position said donor punch is in position over said recipient block holder and in alignment with said Z axis.

* * * * *